(12) United States Patent
Warner et al.

(10) Patent No.: US 9,078,578 B2
(45) Date of Patent: Jul. 14, 2015

(54) SYSTEM AND METHOD FOR OPTIMIZING ELECTROCARDIOGRAPHY STUDY PERFORMANCE

(71) Applicants: Adrian F. Warner, Wauwatosa, WI (US); Daniel R. Schneidewend, Wauwatosa, WI (US); Rodger F. Schmit, Wauwatosa, WI (US); Timothy P. Stiemke, Wauwatosa, WI (US)

(72) Inventors: Adrian F. Warner, Wauwatosa, WI (US); Daniel R. Schneidewend, Wauwatosa, WI (US); Rodger F. Schmit, Wauwatosa, WI (US); Timothy P. Stiemke, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 10 days.

(21) Appl. No.: 13/933,202

(22) Filed: Jul. 2, 2013

(65) Prior Publication Data
US 2015/0011901 A1      Jan. 8, 2015

(51) Int. Cl.
A01B 5/04      (2006.01)
A61B 5/04      (2006.01)

(52) U.S. Cl.
CPC .................. *A61B 5/04017* (2013.01)

(58) Field of Classification Search
USPC ........................................................ 600/509
See application file for complete search history.

(56) References Cited

U.S. PATENT DOCUMENTS

| | | |
|---|---|---|
| 3,476,103 A | 11/1969 | Stenger et al. |
| 3,498,288 A | 3/1970 | Max et al. |
| 3,757,778 A | 9/1973 | Graham |
| 4,191,195 A | 3/1980 | Miller |
| 4,494,551 A | 1/1985 | Little, III et al. |
| 4,890,630 A | 1/1990 | Kroll et al. |
| 4,981,141 A | 1/1991 | Segalowitz |
| 5,002,063 A | 3/1991 | Haner |
| 5,020,541 A | 6/1991 | Marriott |
| 5,022,404 A | 6/1991 | Hafner |
| 5,392,784 A | 2/1995 | Gudaitis |
| 5,582,181 A | 12/1996 | Ruess |
| 5,632,280 A | 5/1997 | Leyde et al. |
| 5,713,365 A | 2/1998 | Castelli |
| 5,788,644 A | 8/1998 | Donehoo et al. |
| 5,902,249 A | 5/1999 | Lyster |
| 6,259,246 B1 | 7/2001 | Ward |
| 6,287,328 B1 | 9/2001 | Snyder et al. |
| 6,741,132 B2 | 5/2004 | Renous et al. |
| 7,088,166 B1 | 8/2006 | Reinschmidt et al. |
| 7,317,161 B2 | 1/2008 | Fukuda |
| 7,737,724 B2 | 6/2010 | Snyder et al. |
| 7,761,845 B1 | 7/2010 | Perrin et al. |
| 7,765,095 B1 | 7/2010 | Nemecek |
| 7,770,113 B1 | 8/2010 | Anderson et al. |
| 7,774,190 B1 | 8/2010 | Nemecek |
| 7,825,688 B1 | 11/2010 | Snyder et al. |
| 7,844,437 B1 | 11/2010 | Ogami et al. |

(Continued)

OTHER PUBLICATIONS

E. Alnasser, Compensated Transconductance Driven-Right-Leg Circuit; IET Science, Measuremnt and Technology; 2012, vol. 6, Iss. 6, pp. 519-526.*

*Primary Examiner* — Paula J Stice
(74) *Attorney, Agent, or Firm* — Grogan, Tuccillo & Vanderleeden LLP

(57) ABSTRACT

A method for optimizing electronic signal monitoring study performance includes assessing study criteria to determine an appropriate noise reduction circuit and selecting an appropriate noise reduction circuit from a plurality of noise reduction circuits in an electronic signal monitoring system. The study is then conducted using the selected noise reduction circuit.

14 Claims, 4 Drawing Sheets

(56) References Cited

U.S. PATENT DOCUMENTS

| | | |
|---|---|---|
| 7,893,724 B2 | 2/2011 | Moyal et al. |
| D639,437 S | 6/2011 | Bishay et al. |
| 8,026,739 B2 | 9/2011 | Sullam et al. |
| 8,040,266 B2 | 10/2011 | Thiagarajan et al. |
| 8,049,569 B1 | 11/2011 | Wright et al. |
| 8,067,948 B2 | 11/2011 | Sequine |
| 8,069,405 B1 | 11/2011 | Bartz et al. |
| 8,069,428 B1 | 11/2011 | Ogami et al. |
| 8,069,436 B2 | 11/2011 | Snyder et al. |
| 8,076,580 B2 | 12/2011 | Kolasa et al. |
| 8,078,894 B1 | 12/2011 | Ogami |
| 8,078,970 B1 | 12/2011 | Anderson |
| 8,085,067 B1 | 12/2011 | Stiff |
| 8,085,100 B2 | 12/2011 | Brennan |
| 8,089,461 B2 | 1/2012 | Beard et al. |
| 8,092,083 B2 | 1/2012 | Venkataraman et al. |
| 8,103,496 B1 | 1/2012 | Roe et al. |
| 8,103,497 B1 | 1/2012 | Nemecek et al. |
| 8,120,408 B1 | 2/2012 | Sivadasan et al. |
| 8,130,025 B2 | 3/2012 | Kutz |
| 8,149,048 B1 | 4/2012 | Mar |
| 2012/0323132 A1* | 12/2012 | Warner et al. ................. 600/523 |

* cited by examiner

SYSTEM AND METHOD FOR OPTIMIZING ELECTROCARDIOGRAPHY STUDY PERFORMANCE

BACKGROUND

1. Technical Field

Embodiments of the invention relate generally to electronic signal monitoring and more specifically to systems and methods for optimizing electrocardiography study performance.

2. Discussion of Art

Electrocardiography (ECG) studies record the electrical activity and pathways of a heart to identify, measure and diagnose arrhythmias. In particular, such studies measure electrical changes caused by the depolarization of the heart muscle during each heartbeat. To accomplish this, ECGs utilize electrodes that are combined into combinations, the output of which are referred to as a lead.

ECG leads are used in electrophysiology (EP) studies, which assess electrical activity through the use of catheters placed in the heart through veins or arteries. More specifically, surface ECG leads attached to the patient are used as the reference for the intra cardiac signals from the catheters. That is, they provide a voltage reference to the patient for measurement by other leads.

In this context, ECG leads may encounter noise from a variety of sources such as wireless electrical devices. Moreover, EP studies are typically combined with ablation therapy in which a catheter employs radiofrequency energy, for example, to treat arrhythmias. Various medical devices may also attached to a patient during an EP study potentially creating noise. In addition, ECG leads have to measure relatively small electrical signals from the patient, less than 20 uV in some instances. As will be appreciated, given the above considerations, achieving acceptable study recordings may be challenging.

To reduce noise, ECG systems often utilize a circuit design topology derived from a circuit commonly referred to as "driven right leg" or "right leg drive." Right leg drive (RLD) circuitry is used to eliminate common mode interference noise and to ensure that recording system ground tracks with the patient. In general, RLD circuits introduce a signal into right leg of a patient to cancel common mode noise from the electrodes. There are currently several RLD circuit topologies that are configured and/or tuned for specific study conditions. As will be appreciated, however, a particular RLD circuit may offer suboptimal performance when it is used in an application that differs from the specific study conditions for which the circuit was originally configured/tuned, or when study conditions change.

It is desirable to provide an ECG system with user selectable and/or modifiable circuit topologies to optimize system performance in a wide variety of study conditions.

BRIEF DESCRIPTION

In an embodiment, a method for optimizing electronic signal monitoring study performance is provided. The method includes assessing study criteria to determine an appropriate noise reduction circuit and selecting an appropriate noise reduction circuit from a plurality of noise reduction circuits in an electronic signal monitoring system. The study is then conducted using the selected noise reduction circuit.

In an embodiment, a method for optimizing electrocardiography study performance is provided. The method includes assessing study criteria to determine an appropriate right leg drive circuit and then selecting an appropriate right leg drive circuit from a plurality of right leg drive operatively connected to an electrocardiography amplifier. The study is then conducted using the selected right leg drive circuit.

In an embodiment, system for optimizing electrocardiography study performance is provided. The system includes an amplifier, a controller operatively connected to the amplifier, and a plurality of noise reduction circuits operatively connected to the controller and amplifier. The controller may be used to select or modify one of the noise reduction circuits given study criteria.

DRAWINGS

The present invention will be better understood from reading the following description of non-limiting embodiments, with reference to the attached drawings, wherein below:

DETAILED DESCRIPTION

Figure 1:
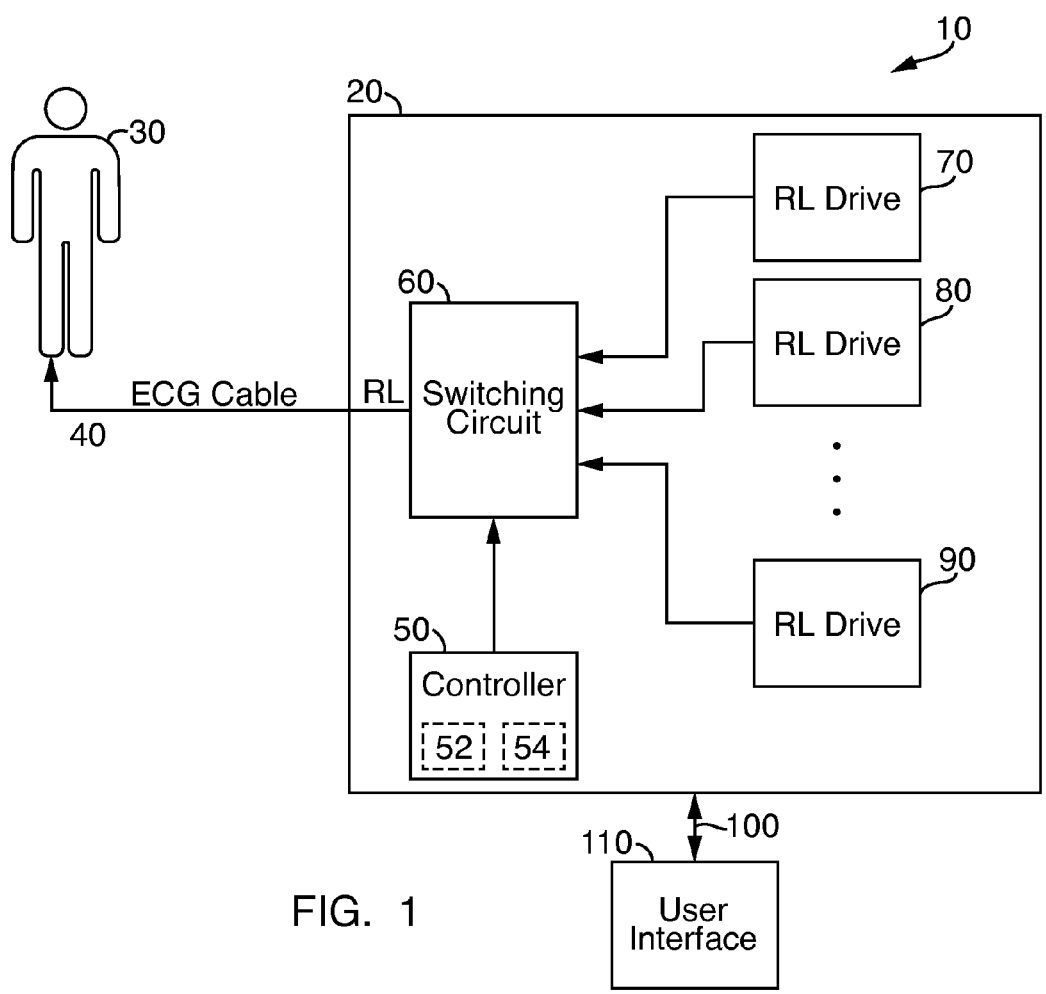
FIG. 1 is a schematic illustration of a system for optimizing electrocardiography study performance in accordance with an embodiment of the present invention.

Reference will be made below in detail to exemplary embodiments of the invention, examples of which are illustrated in the accompanying drawings. Wherever possible, the same reference characters used throughout the drawings refer to the same or like parts. Although embodiments of the present invention are described as intended for use with electrocardiograph systems, it will be appreciated that embodiments may be adapted for use with other electronic signal monitoring systems that utilize circuit topologies to reduce noise, wander, and/or otherwise increase performance. These may include, but are not limited to, electro encephalogram, electromyogram, electroneurogram, and electromyogram systems.

Moreover, embodiments of the system can be used with various ECG signal acquisition applications such as ECG monitoring in an EP study, stress test ECG, resting ECG, exercise ECG, patient monitoring, defibrillators, etc., involving sensitive electrical signal recording and processing. Sources of noise may include, but are not limited to, the use of ablation equipment, the attachment of multiple medical devices to a subject, ungrounded electrical extension cords, electrical sockets, high-energy consumption equipment, and the like. Embodiments of the inventive system are intended for use in testing subjects, which, as will be appreciated, may be animals or humans.

Referring now to FIG. 1, an embodiment of the system is depicted. As shown, the system 10 includes an electronic signal monitoring system, which in the depicted embodiment is an ECG amplifier 20, which is operatively attached to a subject 30 through an ECG cable 40. As shown, the ECG cable 40 is attached to the subject's right leg for use with various RLD circuits. The amplifier 20 includes a controller 50 and a switching circuit 60. The switching circuit 60 is operatively connected to multiple noise reduction circuits, which, in the depicted embodiment, are RLD circuits 70, 80 and 90. While the illustrated embodiment includes three circuits, other embodiments may include more than three circuits, other embodiments may include two circuits, and yet other embodiments may include a single modifiable circuit.

In an embodiment, the controller 50 includes a processor 52 that executes a program of instructions to select an appropriate noise reduction circuit. The controller 50 may also include, or otherwise be connected to, memory storage 54, such as a solid-state drive. The memory storage 54 contains the program of instructions used to execute embodiments of the inventive method and system. In certain embodiments, the controller 50 may be external to the amplifier 20 and coupled to the amplifier via a link, e.g., cable or wireless connection. In certain embodiments, the controller may be user programmable.

The controller 50 is operatively connected to a switching circuit 60 such that the controller 50 can control the switching circuit to select one of the connected noise reduction circuits 70, 80, 90. In embodiments, the switching circuit may be a low impedance solid-state switch, or photomos relay, or electro-mechanical relay, or other switching circuit. In other embodiments, other switching circuits may be utilized.

The system 10 further includes a user interface operatively connected to the amplifier 20 via line 100. As will be appreciated, the user interface 110 allows a user to select or modify a specific noise reduction circuit 70, 80, 90 such that an optimal or "appropriate" circuit may be used for specific subject study criteria or test circumstances. "Study criteria" as used herein refers generally to potential sources of noise or baseline wander including, but not limited to, the use of ablation equipment, the attachment of multiple medical devices to a subject, ungrounded electrical extension cords, electrical sockets, high-energy consumption equipment, and the like. Study criteria also include the type of study, e.g., ECG or other type of electronic signal monitoring systems, as well as desired levels of signal definition. As used herein, "appropriate" noise reduction circuits are those that will achieve optimal performance, e.g., signal measurement, given the study criteria that are on hand at the time the study is to be completed.

Referring back to the system 10, in certain embodiments, the interface 110 may be a Graphical User Interface, such as a computer monitor and keyboard, touch screen, or other human computer interface. In embodiments where the controller 50 is separate from amplifier 20, the interface 110 may be directly connected to the controller 50.

Figure 2:
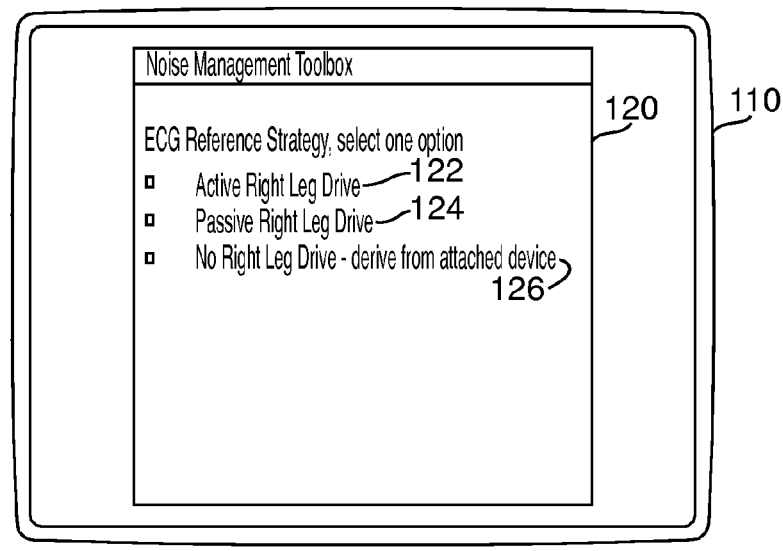
FIG. 2 is a screen capture of a graphical user interface in accordance with an embodiment of the present invention.
Figure 3:
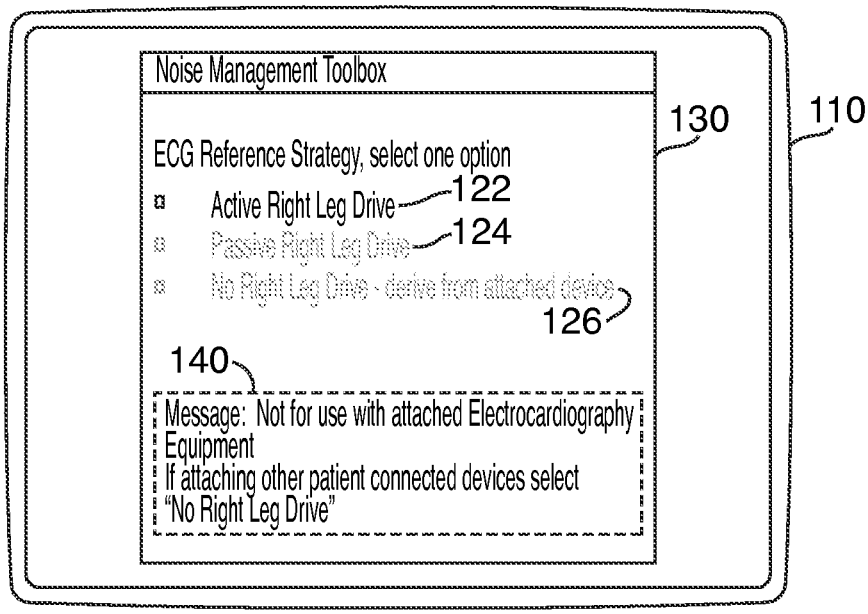
FIG. 3 is a screen capture of a graphical user interface in accordance with another embodiment of the present invention.
Figure 4:
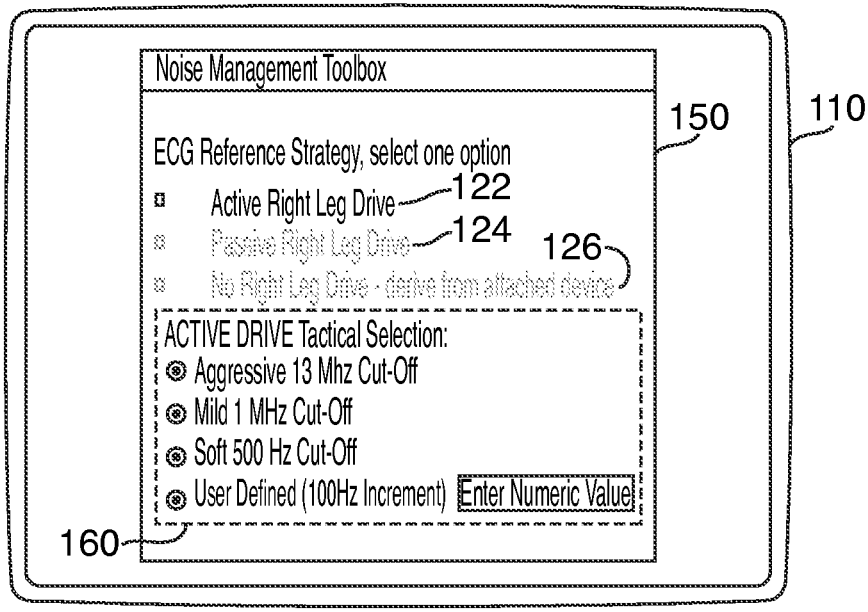
FIG. 4 is a screen capture of a graphical user interface in accordance with another embodiment of the present invention.

Referring now to FIGS. 2-4, screen captures from an exemplary interface 110 are depicted. In particular, in the embodiment shown in FIG. 2, a user is presented with three noise reduction circuit options. These include active RLD 122, passive RLD 124 and no RLD 126. As used herein, "active" circuits are those that contain transistors such as power supplies, amplifiers or converters. "Passive" circuits refer to circuits containing only passive components such as resistors, capacitors and inductors.

In the embodiment of FIG. 2, a user can select from between active, passive and no RLD circuits. Accordingly, a user can select a specific circuit, i.e., a reference strategy, most appropriate for a specific subject's study criteria. In this embodiment, a user may opt for no RLD circuit, if for example, another reference can be employed, or an active or passive RLD circuit where appropriate. As will be appreciated, the determination of what circuit is most appropriate will typically be based on the study criteria mentioned above. A user may also select a circuit that provides greater signal definition at the expense of noise depending on study conditions.

As shown in FIG. 3, embodiments of the invention may include a guidance option where a user is provided with prompts to guide the user's selection of a reference. As depicted, the interface 110 may provide an alert 140 based upon the subject study criteria which may entered by the user into the controller 50 via the interface 110 at the beginning of a study. For example, in an embodiment, a user may be provided with an alert when certain noise functions are detected, such as when baseline wander exceeds a certain preset or user defined threshold.

Embodiments may also provide guidance when an inappropriate selection is made. For example, if a user selects No Right Leg Drive when there is no other equipment attached to the subject, the user may receive an alert to this effect. A user may also be presented with a questionnaire or separate input screen through interface 140 into which relevant information regarding the study may be entered. In certain embodiments, the controller may also provide study performance feedback, after a study has been run, to the user via the user interface 110. In this fashion, the user can then modify or change the initial circuit selection.

In embodiments, there may be multiple passive circuits that are each tuned differently. Here, a user may choose a passive circuit based on frequency response curve. Similarly, in other embodiments, a user may choose from three or more active right leg drive circuits, each having a different tuned performance.

In some embodiments, a user may be initially presented with the three-circuit choice of FIG. 2, or similar selection, via interface 110. Once an initial selection has been entered, such as Active Right Leg Drive, the user may then be presented with a second set of choices in which the user can select a specifically tuned Active RLD Circuit or refine the selected Active RLD circuit.

Referring now to FIG. 4, a modifiable or tunable circuit may be employed. That is, the user can select a specific circuit such as, Active Right Leg Drive 122. Once the selection is made, the user may then be presented with an input screen 160 into which they can tune the circuit by selecting or entering, for example, a specific frequency of the cut-off for the circuit. As will be appreciated, in embodiments, circuits may be tuned and then re-tuned in real time based upon initial study results. The ability to tune the Active RLD circuit response allows users to control and potentially minimize interactions between multiple devices attached to a single subject.

Figure 5:
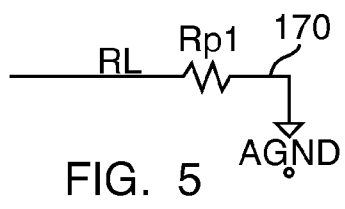
FIG. 5 is a diagram of an exemplary passive right leg drive circuit for use with an embodiment of the present invention.
Figure 6:
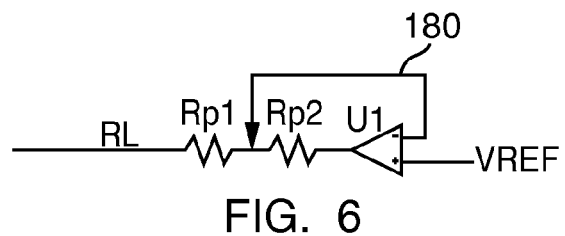
FIG. 6 is a diagram of an exemplary active right leg drive circuit for use with an embodiment of the present invention.
Figure 7:
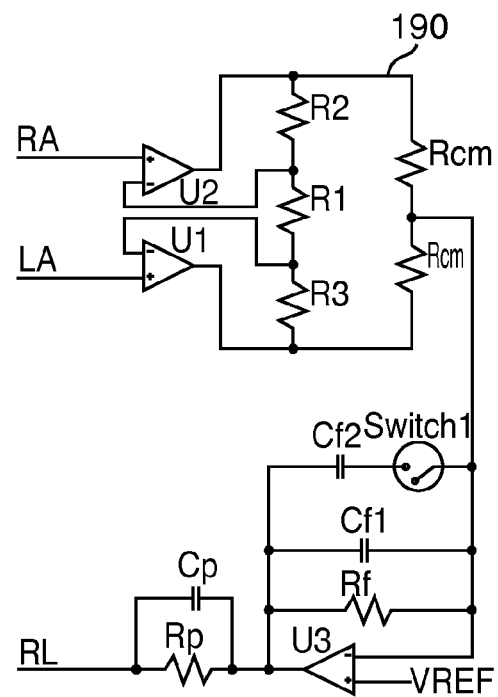
FIG. 7 is a diagram of an exemplary active right leg drive circuit with operator selectable response characteristics for use with an embodiment of the present invention.

FIGS. 5-7 provide non-limiting examples of noise reduction circuits that may be employed in embodiments of the invention. In particular, FIG. 5 is a diagram of a passive RLD circuit 170. FIG. 6 is a diagram of an active RLD circuit 180. Finally, FIG. 7 is an example of an active RLD 190 with operator selectable response characteristics. It should be appreciated, however, that other RLD circuits and potentially non-RLD noise reduction circuits, may be used in embodiments of the invention.

Figure 8:
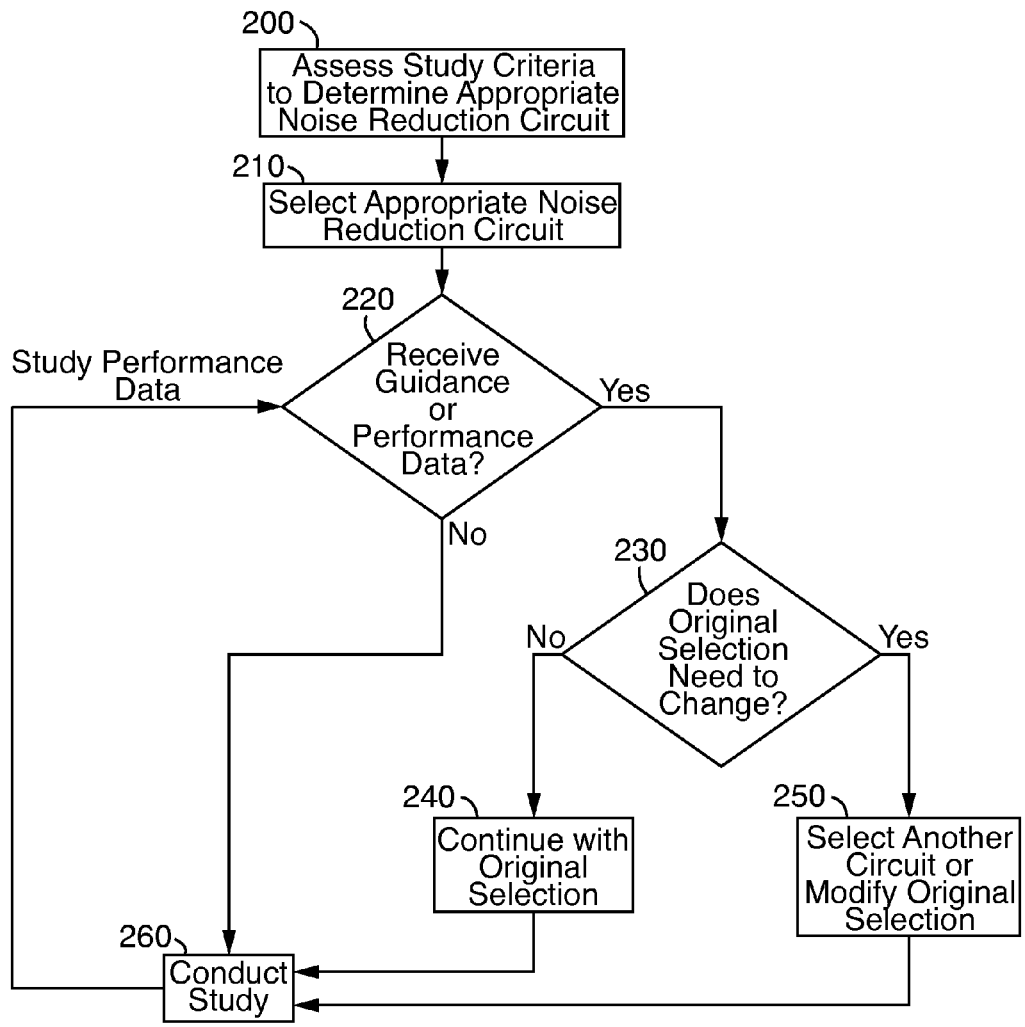
FIG. 8 is a flowchart illustrating a method for optimizing electrocardiography study performance in accordance with an embodiment of the present invention.

Referring now to FIG. 8, a method for optimizing electronic signal monitoring study performance according to an embodiment of the invention is shown. In the method, at step 200, study criteria are initially assessed to determine an appropriate noise reduction circuit. An appropriate circuit is then selected at step 210 from among a plurality of circuits in an electronic monitoring system, such as an ECG amplifier. At this point, the user may receive guidance from the controller via the user interface regarding the appropriateness of the initial selection. For example, if the user selected No Right Leg Drive and no other attached device was present, the user may be notified to select again. Alternatively, the user may receive performance data at step 220, assuming that at least one study has been conducted with the selected circuit (step 260).

If guidance or performance data is received the user then determines whether the original circuit selection needs to change (step 230). If not, the user continues with the original selection (step 240) and the study is conducted (step 260). If the original selection needs to change, then the user can select another circuit, e.g., a passive right leg drive, or the user may modify the original selection, e.g., change the response characteristics of a selected right leg drive circuit (step 250), and then conduct the study (step 260).

It is anticipated that in certain embodiments the user can change circuit selections during a study. That is, in multi-equipment procedures, the user can quickly disable the reference circuit as needed by selecting No Right Leg Drive. The user can also adjust selected reference circuits where appropriate. In this way, amplifier performance is not potentially compromised by being limited to a single reference circuit.

In an embodiment, a method for optimizing electronic signal monitoring study performance includes assessing study criteria to determine an appropriate noise reduction circuit, selecting an appropriate noise reduction circuit from a plurality of noise reduction circuits in an electronic signal monitoring system, and conducting the study using the selected noise reduction circuit. The selected noise reduction circuit may then be modified to increase its performance. The method may further include receiving information regarding the choice or performance of the selected noise reduction circuit and, in response, selecting a new noise reduction circuit, or modifying the noise reduction circuit originally selected, based on the received information, and then conducting the study with the new or modified noise reduction circuit.

In embodiments, the electronic signal monitoring study is an electocardiography study and the electronic signal monitoring system is an electrocardiography amplifier. The noise reduction circuits are right leg drive circuits and can include at least one active right leg drive circuit and/or at least one passive right leg drive circuit.

In an embodiment, a method for optimizing electrocardiography study performance include assessing study criteria to determine an appropriate right leg drive circuit, selecting an appropriate right leg drive circuit from a plurality of right leg drive operatively connected to electrocardiography amplifier, and conducting the electrocardiography study using the selected right leg drive circuit. The method also includes modifying the selected right leg drive circuit to increase its performance prior to conducting the electrocardiography study. The method further includes receiving information regarding the choice or performance of the selected right leg drive circuit and selecting a new right leg drive circuit, or modifying the right leg drive circuit originally selected, based on the received information, and then conducting the study with the new or modified right leg drive circuit.

In an embodiment, a system for optimizing electrocardiography study performance includes an amplifier, a controller operatively connected to the amplifier, a plurality of noise reduction circuits operatively connected to the controller and amplifier. The controller may be used to select or modify one of the noise reduction circuits given study criteria. The plurality of noise reduction circuits are operatively connected to the controller via a switching circuit. The system also includes a user interface operatively connected to the controller. The controller includes a processor and memory storage containing a program of instructions allowing a user of the system to select a noise reduction circuit that is appropriate given study criteria.

In embodiments, the noise reduction circuits are right leg drive circuits and may include at least one active right leg drive circuit. The controller provides study performance data to a user via the user interface so that a user can assess whether a new noise reduction circuit should selected or whether the selected circuit should be modified.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. §122, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method for optimizing performance of an electronic signal monitoring study comprising:
   assessing study criteria to determine an appropriate noise reduction circuit;
   selecting via a computer-implemented user interface an appropriate noise reduction circuit from a plurality of noise reduction circuits in an electronic signal monitoring system, wherein at least one of the plurality of noise reduction circuits is a right leg drive circuit;
   connecting ECG cables from the electronic signal monitoring system to a patient; and
   obtaining a noise reduced ECG trace through operation of the electronic signal monitoring system using the noise reduction circuit.

2. A method for optimizing performance of an electronic signal monitoring study comprising:
   assessing study criteria to determine a right leg drive circuit;
   selecting via a computer-interface an appropriate right leg drive circuit from a plurality of right leg drive circuits operatively connected to an electrocardiography amplifier;
   connecting ECG cables from the electrocardiography amplifier to a patient; and obtaining a noise reduced ECG trace through operation of the electrocardiography amplifier using the selected right leg drive circuit.

3. The method of claim 2 further comprising:
   modifying the selected right leg drive circuit to increase its performance.

4. The method of claim 2 further comprising:
   receiving information regarding the choice or performance of the selected right leg drive circuit.

5. The method of claim 4 further comprising:
   selecting a new right leg drive circuit, or modifying the right leg drive circuit originally selected, based on the received information; and
   conducting the study with the new or modified right leg drive circuit.

6. The method of claim 2 wherein the right leg drive circuits include at least one active right leg drive circuit.

7. The method of claim 2 wherein the right leg drive circuits include at least one passive right leg drive circuit.

8. A system for optimizing electrocardiography study performance comprising:
   an amplifier;
   a controller operatively connected to the amplifier;
   A plurality of noise reduced circuits operatively connected to the controller and amplifier, wherein at least one of the plurality of noise reduction circuits is a right leg drive circuit; and
   ECG cables operatively connected to the amplifier for connection to a patient;
   wherein the controller may be used to select or modify one of the noise reduction circuits given study criteria.

9. The system of claim 8 wherein the plurality of noise reduction circuits are operatively connected to the controller via a switching circuit.

10. The system of claim 8, further comprising a user interface operatively connected to the controller.

11. The system of claim 10 wherein the controller provides study performance data to a user via the user interface so that a user can assess whether a new noise reduction circuit should selected or whether the selected circuit should be modified.

12. The system of claim 8 wherein the noise reduction circuits are right leg drive circuits.

13. The system of claim 12 wherein the right leg drive circuits include at least one active right leg drive circuit.

14. The system of claim 8 wherein the controller includes a processor and memory storage containing a program of instructions allowing a user of the system to select a noise reduction circuit that is appropriate given study criteria.

* * * * *